(12) United States Patent
Nakajima

(10) Patent No.: US 12,138,125 B2
(45) Date of Patent: Nov. 12, 2024

(54) ULTRASONIC DIAGNOSTIC APPARATUS

(71) Applicant: Hitachi, Ltd., Tokyo (JP)

(72) Inventor: Shinji Nakajima, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 540 days.

(21) Appl. No.: 17/220,090

(22) Filed: Apr. 1, 2021

(65) Prior Publication Data
US 2022/0079562 A1    Mar. 17, 2022

(30) Foreign Application Priority Data
Sep. 14, 2020 (JP) .................... 2020-153564

(51) Int. Cl.
*A61B 8/00* (2006.01)
(52) U.S. Cl.
CPC .............. *A61B 8/467* (2013.01); *A61B 8/44* (2013.01); *A61B 8/4405* (2013.01)
(58) Field of Classification Search
None
See application file for complete search history.

(56) References Cited

U.S. PATENT DOCUMENTS

| | | | | |
|---|---|---|---|---|
| 9,451,931 B2* | 9/2016 | Ninomiya | ............ | A61B 8/4411 |
| 2011/0224544 A1* | 9/2011 | Ahn | ............ | A61B 8/4405 |
| | | | | 600/437 |
| 2013/0021732 A1* | 1/2013 | Nakajima | ............ | A61B 8/54 |
| | | | | 361/679.01 |
| 2013/0027858 A1 | 1/2013 | Nakajima | | |
| 2015/0105660 A1* | 4/2015 | Ninomiya | ............ | A61B 8/4427 |
| | | | | 600/437 |
| 2015/0342562 A1 | 12/2015 | Messina et al. | | |
| 2017/0020280 A1* | 1/2017 | Chuang | ............ | F16M 11/24 |

(Continued)

FOREIGN PATENT DOCUMENTS

| | | |
|---|---|---|
| CN | 102917651 A | 2/2013 |
| CN | 203147212 U | 8/2013 |
| CN | 203280409 U | 11/2013 |

(Continued)

OTHER PUBLICATIONS

Chinese Office Action received in corresponding Chinese Application No. 202110371738.9 dated Jun. 29, 2023.

(Continued)

*Primary Examiner* — Katherine L Fernandez
(74) *Attorney, Agent, or Firm* — MATTINGLY & MALUR, PC

(57) ABSTRACT

The following wires are connected to an actuator via a wire relay mechanism: the wire which acts to move a gas spring which restricts a movement of a parallel linkage which performs an up-down movement of the operation panel, the wire which acts to move a first lock pin which restricts a movement of a rotary pole which performs a first rotational movement of the operation panel, the wire which acts to move a second lock pin which restricts a movement of a mounting unit which performs a second rotational movement of the operation panel, and the wire which acts to move a third lock pin which restricts a movement of a slidable plate which performs a front-rear movement of the operation panel.

8 Claims, 12 Drawing Sheets

(56) References Cited

U.S. PATENT DOCUMENTS

2018/0168547 A1    6/2018  Kim et al.

FOREIGN PATENT DOCUMENTS

| | | | |
|---|---|---|---|
| CN | 104135940 | A | 11/2014 |
| CN | 104869909 | A | 8/2015 |
| CN | 210941461 | U | 7/2020 |
| EP | 3053526 | A1 | 8/2016 |
| JP | 03-138997 | A | 6/1991 |
| JP | 05-253223 | A | 10/1993 |
| JP | 2004-00062 | A | 1/2004 |
| JP | 2008-067794 | A | 3/2008 |
| JP | 2008-179170 | A | 8/2008 |
| JP | 2011-142939 | A | 7/2011 |
| JP | 2011-245041 | A | 12/2011 |
| JP | 2013-121425 | A | 6/2013 |
| JP | 2016-501097 | A | 1/2016 |
| KR | 20090070584 | A | 7/2009 |
| WO | 2017/088108 | A1 | 6/2017 |

OTHER PUBLICATIONS

Chinese Office Action received in corresponding Chinese Application No. 202110371738.9 dated Jan. 11, 2024.
Japanese Office Action received in corresponding Japanese Application No. 2020-153564 dated Jan. 23, 2024.
Chinese Office Action received in corresponding Chinese Application No. 202110371738.9 dated May 6, 2024.
Chinese Office Action received in corresponding Chinese Application No. 202110371738.9 dated Aug. 26, 2024.

* cited by examiner

ULTRASONIC DIAGNOSTIC APPARATUS

CROSS REFERENCE TO RELATED APPLICATION

This application claims priority to Japanese Patent Application No. 2020-153564 filed on Sep. 14, 2020, which is incorporated herein by reference in its entirety including the specification, claims, drawings, and abstract.

TECHNICAL FIELD

The present specification discloses an ultrasonic diagnostic apparatus, in particular, an ultrasonic diagnostic apparatus including an operation panel which receives instructions input by an operator.

BACKGROUND

A general ultrasonic diagnostic apparatus used for medical purposes includes an apparatus body which performs ultrasonic image forming processes, a main display which displays ultrasonic images and the like, and an operation panel which receives instructions input by an operator such as a doctor. The operation panel includes a switch, a pointing device, and a rotary adjustment knob. The operation panel may also include a sub-display which displays various types of information related to instructions to be input.

There are proposed ultrasonic diagnostic apparatuses including an operation panel which is supported by a movable mechanism such that at least either one of the position and orientation of the operation panel is changeable along with movement of the movable mechanism.

For example, JP 2011-245041 A discloses an ultrasonic diagnostic apparatus which includes an operation panel whose position and orientation can be changed by multiple movable mechanisms, including a lift mechanism which changes the height of the operation panel, a right-left slide mechanism which slides the operation panel to the right and left, a front-rear slide mechanism which slides the operation panel to the front and rear, and a rotation mechanism which horizontally rotates the operation panel.

In general, such a movable mechanism which supports the operation panel while allowing a change in the position and/or orientation includes a lock mechanism which can hold the operation panel to maintain the position and/or orientation of the operation panel. The lock mechanism is generally provided for each of the movable mechanisms. For example, JP 2011-245041 A describes an ultrasonic diagnostic apparatus including a lock mechanism which restricts (locks) movement of the right-left slide mechanism and another lock mechanism which restricts movement of the front-rear slide mechanism.

When multiple lock mechanisms are provided, it is desirable that a restriction state of the multiple lock mechanisms can be changed by a single actuator. A change in the restriction state indicates a change between an unrestricted state (unlock state) in which a movement of the movable mechanism is allowed and a restricted state (lock state) in which a movement of the movable mechanism is not allowed.

In the ultrasonic diagnostic apparatus disclosed in JP 2011-245041 A, the restriction state of the right-left slide mechanism and the front-rear slide mechanism can be changed by means of a release lever located in front of the operation panel. However, it is further desired to change the restriction state of more lock mechanisms by manipulating a single actuator, in particular, multiple lock mechanisms including a lift mechanism which can change the height of the operation panel. JP 2011-245041 A does not describe that the above release lever of the ultrasonic diagnostic apparatus can change the restriction state of the lift mechanism. As, conventionally, the restriction state of the lift mechanism is changed by a foot pedal, in the ultrasonic diagnostic apparatus disclosed in JP 2011-245041 A, the restriction state of the lift mechanism can also be assumed to be changed by an actuator such as a foot pedal provided separately from the release lever.

A restriction state of multiple lock mechanisms including the up-down movement mechanism may be changed in accordance with manipulation of a single actuator by using an electric device, such as a motor.

An object of the ultrasonic diagnostic apparatus disclosed in the present specification is to enable changing of the restriction state of multiple lock mechanisms which restrict movement of multiple movable mechanisms in an ultrasonic diagnostic apparatus including the up-down movement mechanism which changes the height of the operation panel, by manipulating a single actuator without using an electric device.

SUMMARY

An ultrasonic diagnostic apparatus according to the present disclosure includes an operation panel which receives an instruction input from an operator, multiple movement mechanisms which change a position or orientation of the operation panel, multiple lock mechanisms which restrict a movement of the movement mechanisms, an actuator, and multiple wires which connect the actuator and the respective multiple lock mechanisms. The multiple movement mechanisms include an up-down movement mechanism which performs an up-down movement to change the height of the operation panel. When the actuator is manipulated by the operator, a restriction state of the multiple lock mechanisms is changed by an effect of the multiple wires.

According to an ultrasonic diagnostic apparatus described in this specification, a restriction state of the multiple lock mechanisms which restrict a movement of the multiple movement mechanisms in the ultrasonic diagnostic apparatus including the up-down movement mechanism which changes the height of the operation panel can be changed by manipulating a single actuator without using any electric devices.

BRIEF DESCRIPTION OF THE DRAWINGS

Embodiments of the present disclosure will be described based on the following figures, wherein.

DESCRIPTION OF EMBODIMENTS

Figure 1:
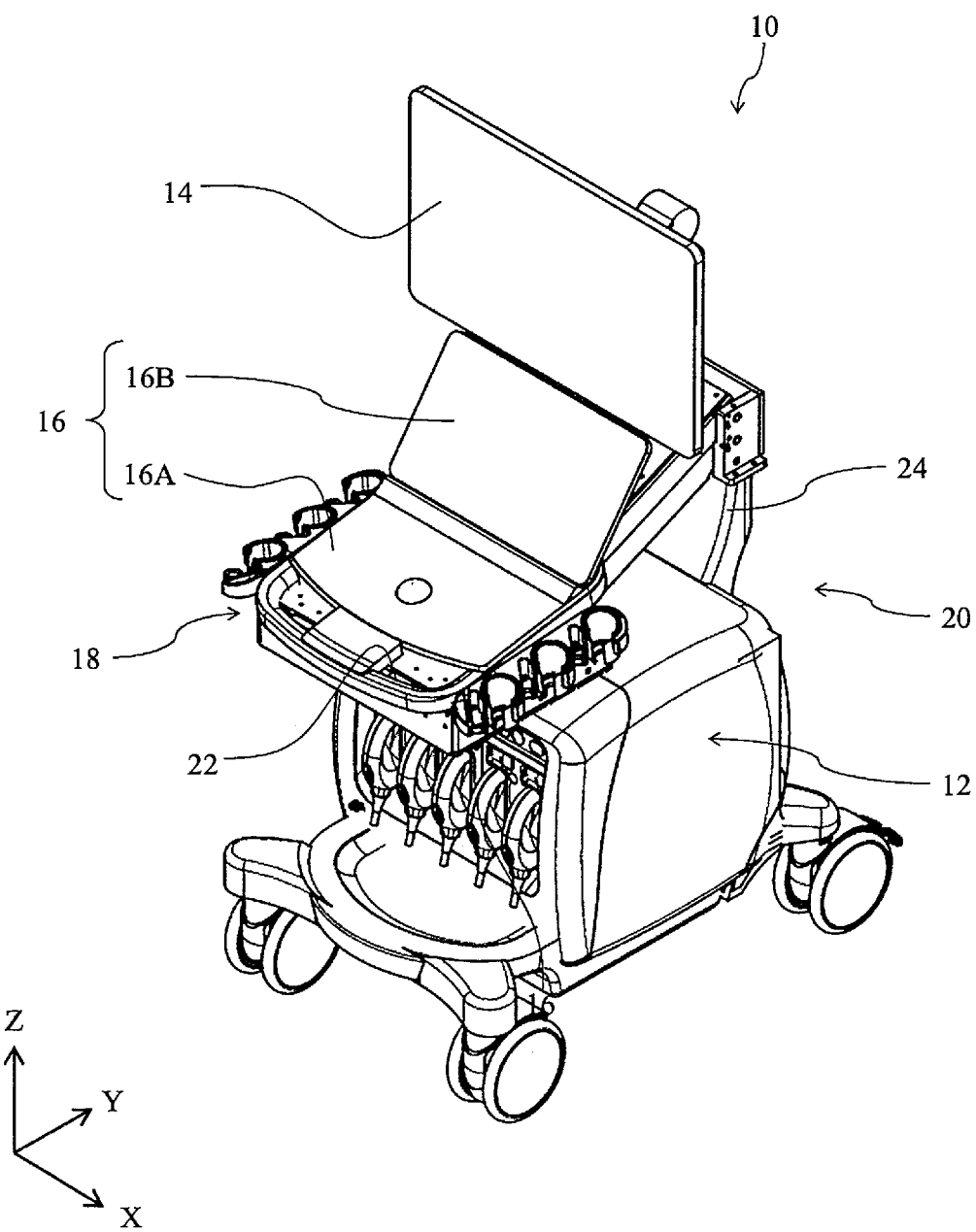
FIG. 1 is a perspective view of an ultrasonic diagnostic apparatus according to an embodiment of the present disclosure.

FIG. 1 is a perspective view of an ultrasonic diagnostic apparatus 10 according to an embodiment of the present disclosure. The ultrasonic diagnostic apparatus 10 includes an apparatus body 12, a main display 14, and an operation panel 16. The ultrasonic diagnostic apparatus 10 also includes an ultrasonic probe (not shown) which is connected to the apparatus body 12 to transmit and receive ultrasonic waves to and from a subject. Throughout the present specification, as shown in FIG. 1, a width direction (also referred to as "right-left direction") of the apparatus body 12 is shown with an arrow X. The arrow X points to the "right" of the apparatus body 12, and the opposite side is "left". A depth direction of the apparatus body 12 is shown with an arrow Y. The arrow Y points to the "rear", and the opposite side is the "front". A height direction of the apparatus body 12 is shown with an arrow Z. The arrow Z points to "up", and the opposite side is "down".

The apparatus body 12 transmits outgoing signals to the ultrasonic probe to instruct the ultrasonic probe to send ultrasonic waves to a subject. The apparatus body 12 also receives incoming signals from the ultrasonic probe to perform an ultrasonic image forming process based on the received signals. The main display 14 displays ultrasonic images formed by the apparatus body 12, and other content.

The operation panel 16 includes a switch, a pointing device, a rotary adjustment knob, and the like so that the operation panel 16 can receive instructions input by an operator such as a doctor. In particular, the operation panel 16 is used by the operator to perform an ultrasonic diagnosis of a subject. In the present embodiment, the operation panel 16 includes a flat console panel 16A on which elements, such as the above mentioned switch, are disposed, and a sub-display 16B which displays various types of information related to instructions to be input. The sub-display 16B is disposed to extend upward from the rear edge of the console panel 16A. The operation panel 16 is disposed on a mounting unit 18, which is a plate-shaped component with an upper surface slightly tilted forward. The console panel 16A is disposed on the upper surface of the mounting unit 18. In this way, the console panel 16A is tilted slightly forward, facilitating the operation of the console panel 16A by an operator. Because the operation panel 16 is disposed on the mounting unit 18, positional relationships between the operation panel 16 and the mounting unit 18 are fixed. Movement and orientation of the mounting unit 18 indicate movement and orientation of the operation panel 16.

The mounting unit 18 is supported by a movable support mechanism 20. The movable support mechanism 20 includes multiple movable mechanisms. The mounting unit 18 is thus movably supported such that at least one of the position and the orientation can be changed. The mounting unit 18 is supported by the movable support mechanism 20 such that the orientation of the mounting unit 18 is changeable, in particular, in a space above the apparatus body 12.

Further, each of movable mechanisms included in the movable support mechanism 20 includes a lock mechanism which restricts movement. The restriction state of the lock mechanism (between an unlock state in which movement is allowed and the lock state in which movement is not allowed) can be changed by an operator. The restriction state change of the multiple lock mechanisms of the movable support mechanism 20 can be performed by an operator by manipulating an actuator 22 disposed at the front of the mounting unit 18 around the lateral center. The respective movement mechanisms, the respective lock mechanisms, and the actuator 22 of the movable support mechanism 20 are described in detail below.

Figure 2:
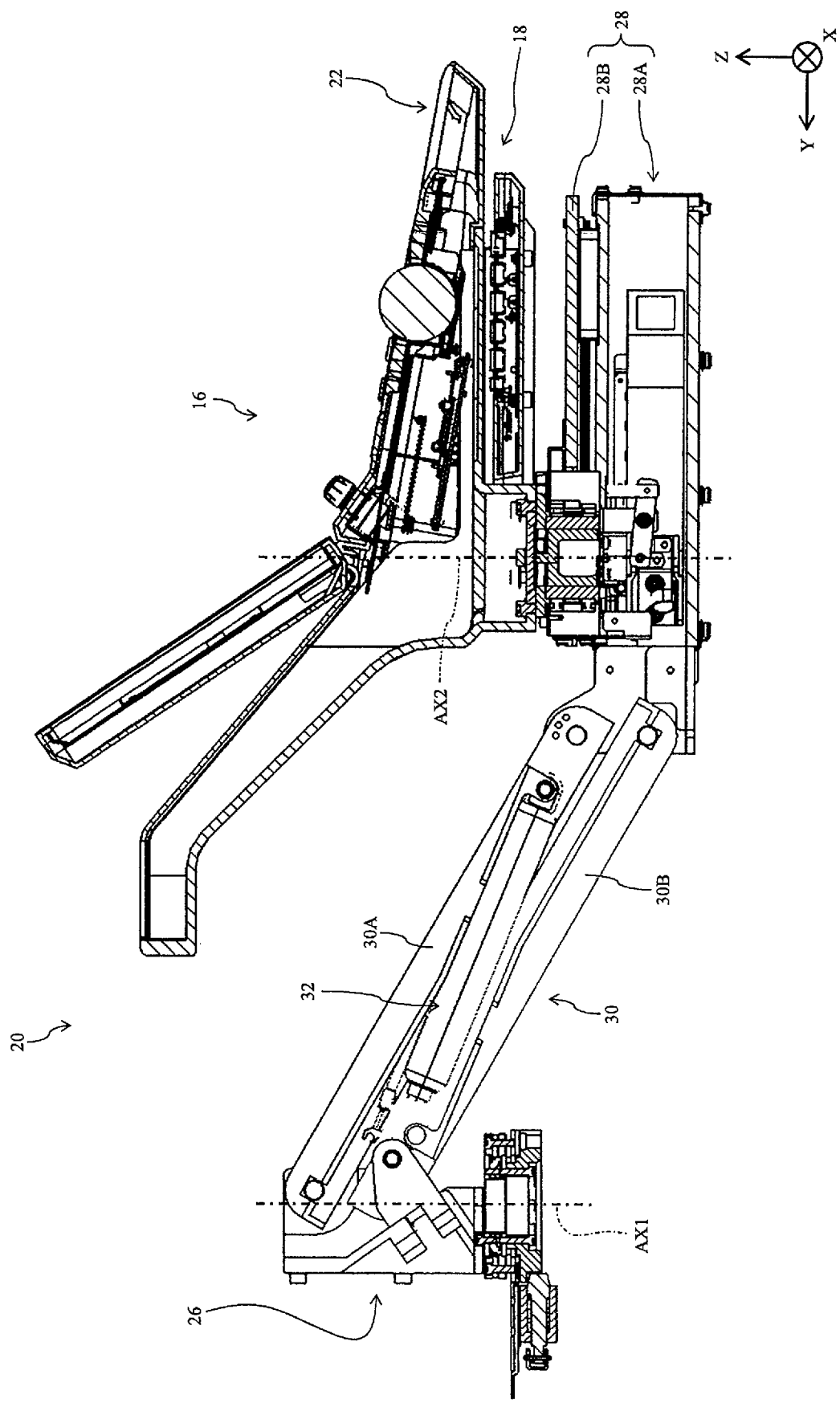
FIG. 2 is a side view (a partial cross sectional view) of a movable support mechanism according to an embodiment of the present disclosure.

FIG. 2 shows a side view of the movable support mechanism 20 according to the present embodiment. FIG. 2 shows a partial cross sectional view. The movable support mechanism 20 mainly includes the above-mentioned mounting unit 18, a fixed pole 24 (refer to FIG. 1, not shown in FIG. 2) which extends upward from the apparatus body 12, a rotary pole 26 connected to the fixed pole 24, a movable base 28 which rotatably supports the mounting unit 18, and a parallel linkage 30 which connects the rotary pole 26 and the movable base 28.

The fixed pole 24 has a column shape and extends upward from around the lateral center at the rear of the apparatus body 12. The fixed pole 24 is fixedly attached to the apparatus body 12. The fixed pole 24 is not a movable mechanism and does not move.

The rotary pole 26 also has a column shape, and extends vertically. The rotary pole 26 is attached on the upper side of the fixed pole 24 such that the lower end of the rotary pole 26 is connected to the upper end of the fixed pole 24. The rotary pole 26 is attached rotatable with respect to the fixed pole 24 (thus, with respect to the apparatus body 12). Specifically, the rotary pole 26 is attached to be rotatable in a horizontal plane about a rotation axis AX1. The rotation axis AX1 is a first vertical axis located away from the mounting unit 18 (thus, away from the operation panel 16).

The movable base 28 has a substantial rectangular shape. Specifically, the movable base 28 includes a box body 28A which has a rectangular shape, and a slidable plate 28B which is horizontally disposed directly above the box body 28A. The slidable plate 28B is slidably attached to the box body 28A such that the slidable plate 28B can slide forward and backward with respect to the box body 28A. FIG. 2 shows the slidable plate 28B at the rearmost position where the slidable plate 28B completely overlaps the upper surface of the box body 28A.

The mounting unit 18 is attached to the slidable plate 28B such that the mounting unit 18 is rotatable in a horizontal plane. Specifically, the mounting unit 18 is attached to be rotatable in a horizontal plane about a rotation axis AX2. The rotation axis AX2 is a second vertical axis which is positioned nearer to the mounting unit 18 (thus, nearer to the operation panel 16) than is the above-mentioned AX1.

The parallel linkage 30 includes two elongated linkages 30A and 30B which are disposed in parallel to each other. One end of the parallel linkage 30 is attached to the rotary pole 26, whereas the other end of the parallel linkage 30 located away in a horizontal direction from the one end is attached at around the lateral center at the rear of the movable base 28. Accordingly, the movable base 28 is supported at a position horizontally away from the rotary pole 26. The parallel linkage 30 is rotatably attached to the rotary pole 26 such that the parallel linkage 30 can rotate in a vertical plane within a predetermined degree. Similarly, the parallel linkage 30 is rotatably attached to the movable base 28 such that the parallel linkage 30 can rotate in a vertical plane within a predetermined degree. The movable base 28 is moved up and down by a rotational movement of the parallel linkage 30 with respect to the rotary pole 26 in a vertical plane, such that the height of the movable base 28 is changed. Along with this movement, the parallel linkage 30 also rotates in a vertical plane with respect to the movable base 28. This maintains the orientation of the movable base 28 (in particular, the slidable plate 28B) to be horizontal when the height of the movable base 28 is changed.

The above elements of the movable support mechanism 20 have a multi-stage structure. Specifically, the mounting unit 18 (thus, the operation panel 16) is rotatable with respect to the slidable plate 28B about the rotation axis AX2. Because the slidable plate 28B itself is movable forward and backward, the mounting unit 18 is also moved forward and backward along with the forward and backward movement of the slidable plate 28B. Further, because the movable base 28 including the slidable plate 28B is moved upward and downward by the rotational movement of the parallel linkage 30, not only the slidable plate 28B but also the mounting unit 18 is moved upward and downward along with the rotational movement of the parallel linkage 30. Furthermore, because the parallel linkage 30 is rotatable in a horizontal plane by the rotational movement of the rotary pole 26 about the rotation axis AX1, the parallel linkage 30, the slidable plate 28B, and the mounting unit 18 rotate in a horizontal plane along with the rotational movement of the rotary pole 26.

As described above, in the movable support mechanism 20 according to the present embodiment, the parallel linkage 30 functions as an up-down movement mechanism which changes the height of the operation panel 16. The rotary pole 26 functions as a first rotational movement mechanism which performs a first rotational movement to rotate the operation panel 16 in a horizontal plane about the rotation axis AX1. The mounting unit 18 functions as a second rotational movement mechanism which performs a second rotational movement to rotate the operation panel 16 in a horizontal plane about the rotation axis AX2. The slidable plate 28B functions as a front-rear movement mechanism which performs a forward/backward movement to change the position of the operation panel 16 in a front-rear direction.

In the movable support mechanism 20, because the rotation axis AX1 of the rotary pole 26 is located away from the operation panel 16, the first rotational movement changes the location of the operation panel 16 along a circumference of a relatively large diameter about the rotation axis AX1. Because the rotation axis AX2 of the mounting unit 18 is located nearer to the operation panel 16 than is the rotation axis AX1 (including the case in which the rotation axis AX2 passes through the operation panel 16), the second rotational movement mainly changes the orientation of the operation panel 16.

Details of the respective movement mechanisms and respective lock mechanisms provided for the movement mechanisms are described below.

Figure 3:
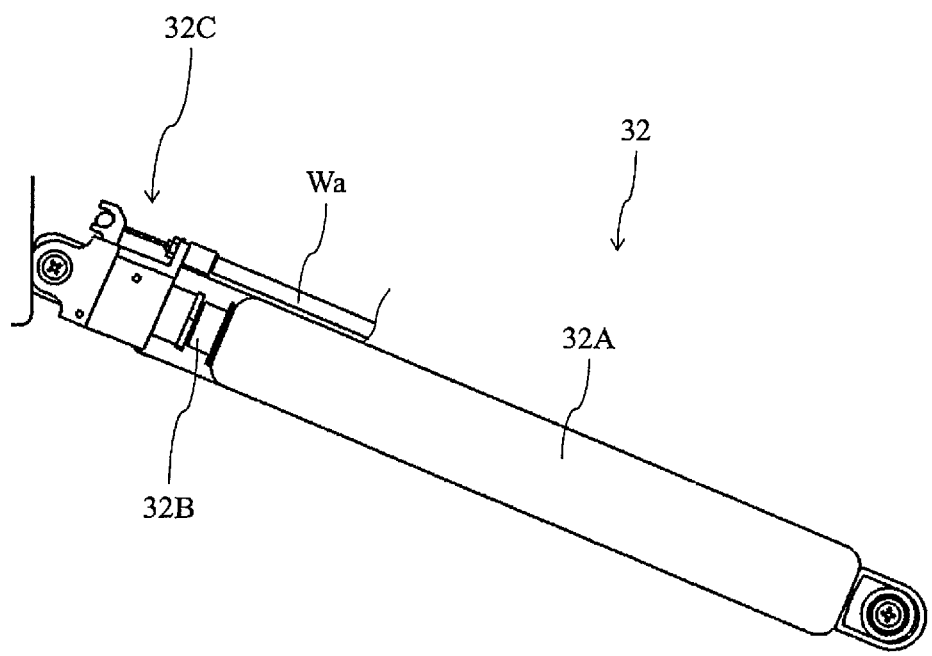
FIG. 3 is a side view of an up-down lock mechanism.

The above parallel linkage 30 used as the up-down movement mechanism includes a gas spring 32 which assists the rotational movement in a vertical plane. FIG. 3 shows a side view of the gas spring 32 which includes a sealed cylinder 32A filled with compressed gas, and a rod 32B inserted in the cylinder 32A. The parallel linkage 30 provides the spring function using a force applied by a reaction force of the compressed gas in the cylinder 32A to the rod 32B in a direction away from the cylinder 32A. The spring function assists the rotational movement of the parallel linkage 30, in particular, the rotational movement to lift the movable base 28.

The gas spring 32 includes a lock 32C which locks the retraction and extension of the rod 32B with respect to the cylinder 32A. When the lock 32C restricts the movement of the rod 32B, the rotational movement of the parallel linkage 30 is restricted. In other words, the gas spring 32 functions as an up-down lock mechanism.

A wire Wa is connected to the gas spring 32. Although detailed description is provided further below, the wire Wa extends to the actuator 22 (refer to FIG. 1 or 2). When the wire Wa is pulled (in FIG. 3, in a lower right direction), the locking action by the lock 32C is released and the restriction of the movement of the rod 32B is thus released. Accordingly, the restriction of rotational movement of the parallel linkage 30 is released. The lock 32C includes a mechanism which applies an urging force by a spring or other device to urge the lock 32C in an upper left direction in FIG. 3. When no pulling force is applied to the wire Wa, the urging force actuates the locking function of the lock 32C to restrict the movement of the rod 32B such that the rotational movement of the parallel linkage 30 is restricted. Because the lock 32C is configured with a two-fulcrum lever, the required force to pull the wire Wa in order to release the lock can be reduced by changing the leverage of the two-fulcrum lever.

Figure 4:
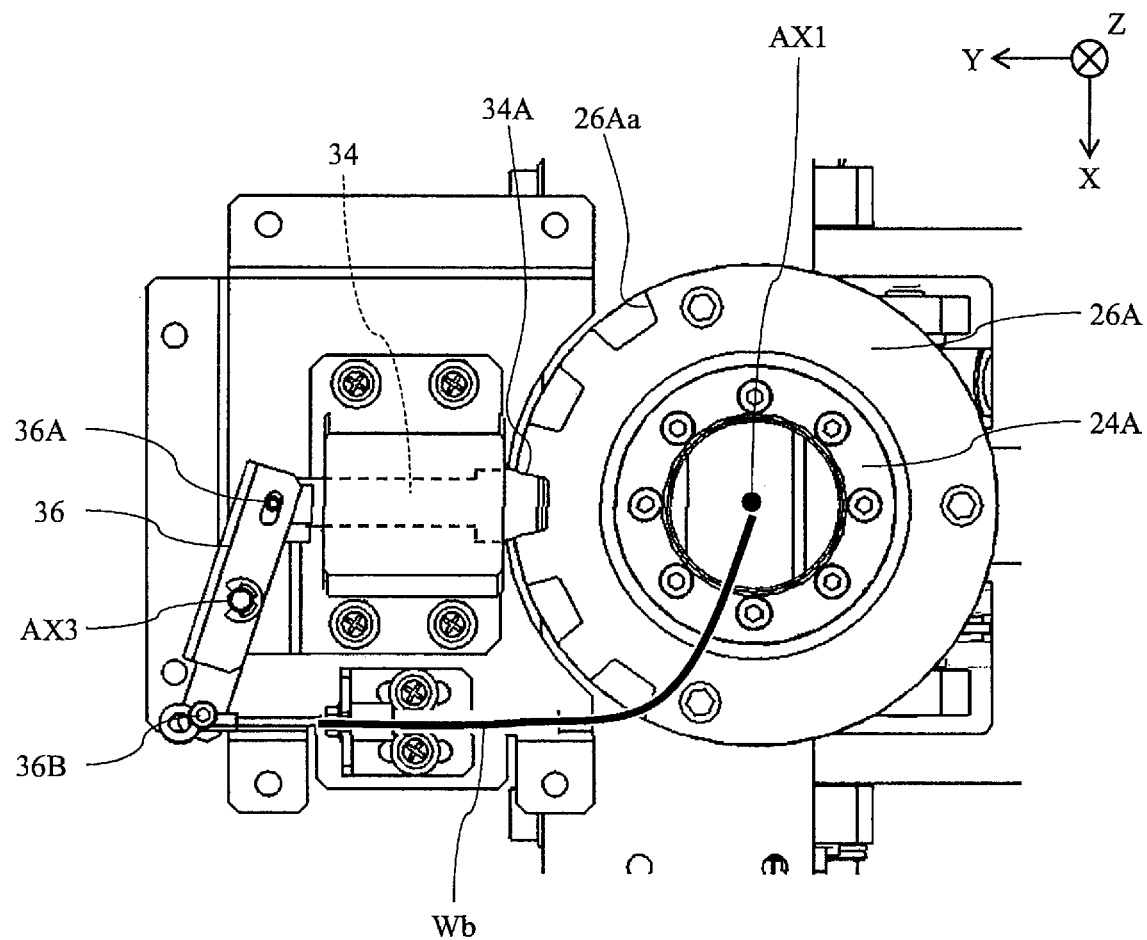
FIG. 4 is a bottom view showing a first rotational movement mechanism and a first rotation lock mechanism.

FIG. 4 shows a bottom view of a joint portion of the fixed pole 24 and the rotary pole 26 used as the first rotational movement mechanism. FIG. 4 shows only a portion of the fixed pole 24.

A cylindrical stator 24A is disposed around an upper lateral surface of the fixed pole 24 such that the stator 24A extends upward therefrom. A cylindrical rotor 26A is disposed around a lower lateral surface of the rotary pole 26 such that the rotor 26A extends downward therefrom. The inner diameter of the rotor 26A is slightly larger than that of the stator 24A. The rotary pole 26 is rotatably coupled to the fixed pole 24 such that the rotary pole 26 is rotatable about the rotation axis AX1 (the circle-center line of the stator 24A and the rotor 26A). Accordingly, when the rotary pole 26 rotates, the rotor 26A rotates on the outer side of the stator 24A.

Multiple first-set lock holes 26Aa are disposed in the lateral surface of the rotor 26A along a circumferential direction.

A first lock pin 34 is provided on a lateral side of the rotor 26A, specifically at the rear (on the left in FIG. 4) in the present embodiment. The first lock pin 34 has an elongated shape extending in a direction along a radial direction of the rotor 26A. The first lock pin 34 is movable along the radial direction of the rotor 26A. Accordingly, the tip of the first lock pin 34 is engageable in one of the first-set lock holes 26Aa located in the lateral surface of the rotor 26A. FIG. 4 shows the first lock pin 34 engaged in one of the first-set lock holes 26Aa. The engagement of the first lock pin 34 in the first-set lock hole 26Aa restricts the rotational movement of the rotor 26A (thus, that of the rotary pole 26). The first-set lock holes 26Aa and the first lock pin 34 function as the first rotation lock mechanism. Because multiple first-set lock holes 26Aa are provided in the lateral surface of the rotor 26A along the circumference, the position to lock the rotary pole 26 is selectable from multiple rotational positions (in other words, orientations).

The proximal end (opposite to the rotor 26A) of the first lock pin 34 is connected to a pin connector 36A of a first relay member 36. In the present embodiment, the pin connector 36A is provided at one end of the first relay member 36. The first relay member 36 has an elongated shape extending along a horizontal direction and is rotatably attached to the fixed pole 24 such that the first relay member 36 is rotatable in a horizontal plane about a vertical rotation axis AX3. A wire Wb is connected to a wire connector 36B of the first relay member 36. In the present embodiment, the wire connector 36B is located at the opposite side of the first relay member 36 from the pin connector 36A. Similarly to the wire Wa, the wire Wb extends to the actuator 22. The wire Wb extends to the actuator 22 through the rotary pole 26 via a central through-hole of the stator 24A (and a central through-hole of the rotor 26A).

When the wire Wb is pulled forward (to the right in FIG. 4), the first relay member 36 rotates counterclockwise in FIG. 4; in other words, the pin connector 36A moves rearward. As a result, the first lock pin 34 moves rearward; that is, in the direction away from the center of the rotor 26A such that the engagement of the first lock pin 34 in the first-set lock hole 26Aa is released and the restriction of the rotational movement of the rotary pole 26 is released. The first lock pin 34 is urged toward the center of the rotor 26A by a spring (not shown). Accordingly, when no pulling force is applied to the wire Wb, the urging force of the spring moves the first lock pin 34 toward the center of the rotor 26A such that the first lock pin 34 engages in the first-set lock hole 26Aa to restrict the rotational movement of the rotary pole 26.

A lateral wall of each of the first-set lock holes 26Aa may include a tilted portion such that the diameter of the hole becomes gradually larger toward the opening of the hole. Correspondingly, the lateral surface of the tip of the first lock pin 34 may include a tapered portion 34A whose diameter becomes gradually smaller from the proximal end toward the distal end. In engagement, the tapered portion 34A of the first lock pin 34 opposes the lateral wall tilted portion of the first-set lock hole 26Aa. This reduces possible friction between the lateral surface of the first lock pin 34 and the lateral wall of the first-set lock hole 26Aa when the tip of the first lock pin 34 pulls out of the first-set lock hole 26Aa. As a result, the required force to pull the wire Wb to release the lock of the first rotational movement is reduced. Furthermore, the lateral-wall tilted portion of the first-set lock hole 26Aa and the tapered portion 34A of the first lock pin 34 are also advantageous in reducing instability of the rotary pole 26 with respect to the fixed pole 24 when locked. This further reduces instability of the operation panel 16, improving operability of the operation panel 16.

Figure 5:
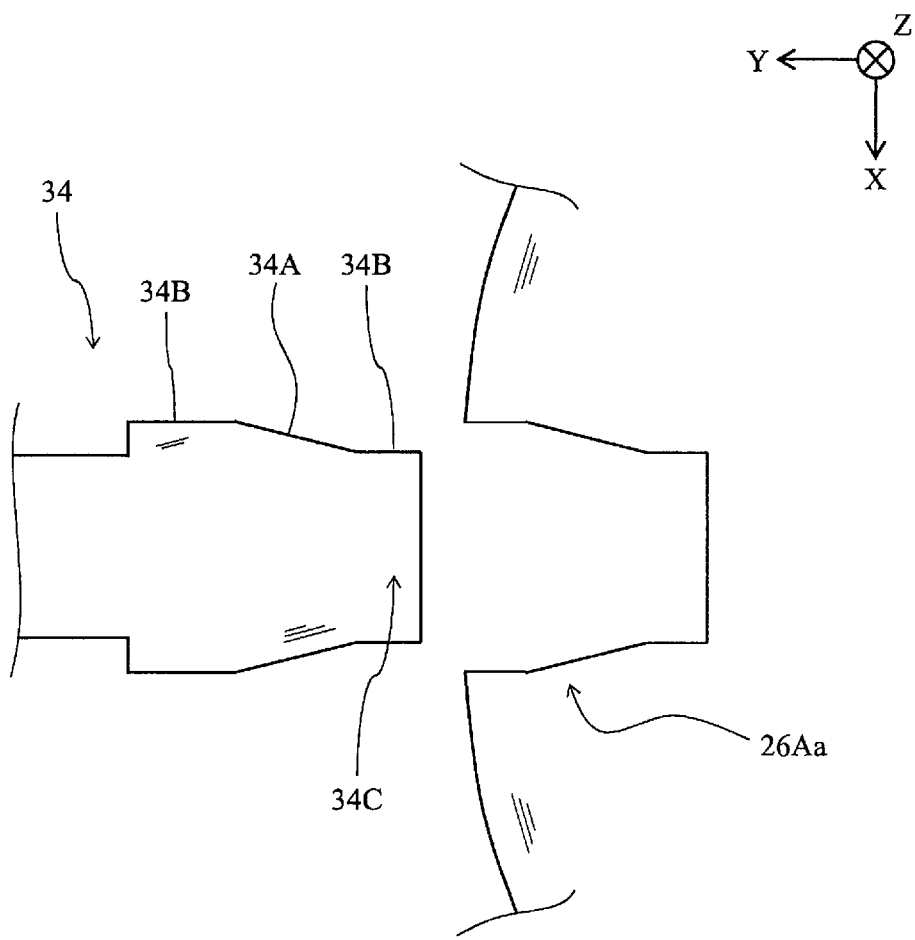
FIG. 5 is an enlarged view of a first lock pin and first-set lock holes.

When the first lock pin 34 includes the tapered portion 34A and a first-set lock hole 26Aa includes the lateral-wall tilted portion, the first lock pin 34 may come into contact with the lateral-wall tilted portion while the first lock pin 34 is moved forward into the first-set lock hole 26Aa. If the rotary pole 26 is rotated by an operator at this timing, the lateral-wall tilted portion may push the tapered portion 34A, applying a force to the first lock pin 34 in a direction to pull the first lock pin 34 out from the first-set lock hole 26Aa. In order to avoid this situation, as shown in FIG. 5, the lateral wall of each first-set lock hole 26Aa may also include lateral-wall non-tilted portions in front of and behind the lateral-wall tilted portion. The lateral-wall non-tilted portions may extend along a hole depth direction to define a constant hole diameter. Correspondingly, the lateral surface of the first lock pin 34 may include straight portions 34B on the proximal and distal sides of the tapered portion 34A such that, in engagement, the straight portions 34B oppose the lateral-wall non-tilted portions. In other words, the first lock pin 34 may include, at the tip, a straight tip portion 34C whose lateral surface is the straight portion 34B having a constant diameter. Because such a structure can reduce a force which may be applied to the first lock pin 34 by the first-set lock hole 26Aa in a direction to pull the first lock pin 34 out from the first-set lock hole 26Aa, the risk of the first lock pin 34 being pulled out can be reduced.

In order to reduce the pulling force required to release the lock of the first rotational movement, in the first relay member 36, the distance between the wire connector 36B and the rotation axis AX3 may be made longer than the distance between the pin connector 36A and the rotation axis AX3. In this way, the pulling force required to release the lock of the first rotational movement (to move the first lock pin 34) can be reduced based on the lever principle.

Figure 6:
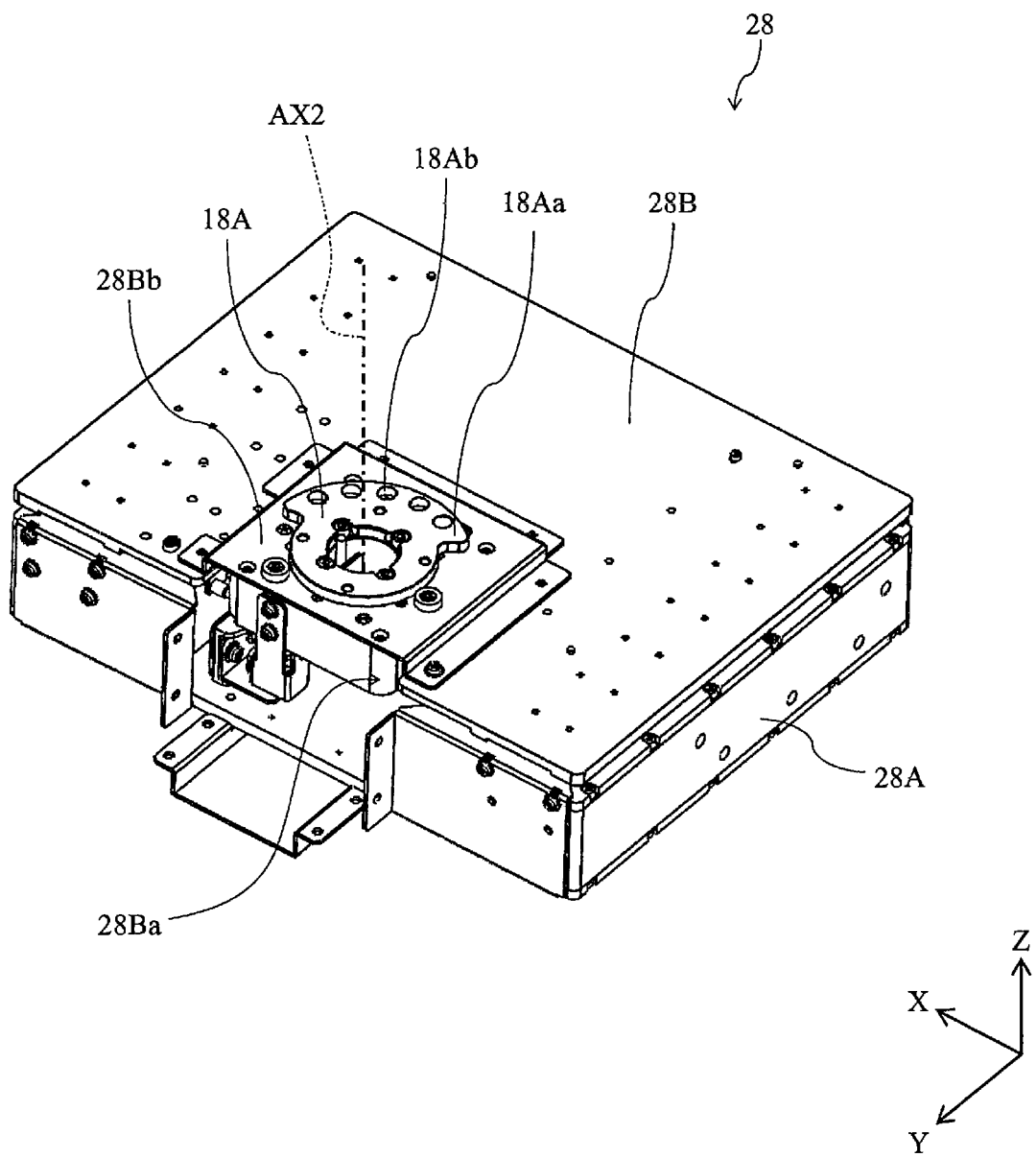
FIG. 6 is a perspective view of a movable base.

FIG. 6 is a perspective diagram showing the movable base 28 and a part of the mounting unit 18. The front (the lower left) and the rear (the upper right) in FIG. 6 are actually the rear and the front, respectively, as shown with the arrows X, Y, and Z.

The slidable plate 28B includes a U-shaped cutout 28Ba at the lateral center on the rear side. In the cutout 28Ba, a stator 28Bb is provided with a hole which extends vertically and has a circular shape in a plan view. A rotor 18A which has a substantial cylindrical shape is provided on the bottom surface of the mounting unit 18; specifically, near the rear edge of mounting unit 18 around the lateral center. The inner diameter of the hole of the stator 28Bb is slightly larger than the outer diameter of the rotor 18A. By engaging the rotor 18A in the hole of the stator 28Bb, the mounting unit 18 can be rotatably attached to the slidable plate 28B about the rotation axis AX2 (the circle-center line of the hole of the stator 28Bb and the cylindrical rotor 18A). Specifically, when the mounting unit 18 rotates, the rotor 18A disposed in the hole of the stator 28Bb also rotates.

The rotor 18A includes, at the upper end, a flange 18Aa which extends to a lateral side of the rotor 18A. The flange 18Aa includes an arch-shaped extended portion about the rotation axis AX2 along the outer circumference. Multiple second-set lock holes 18Ab may be provided in the arch-shaped extended portion of the flange 18Aa around a circumference about the rotation axis AX2

Figure 7:
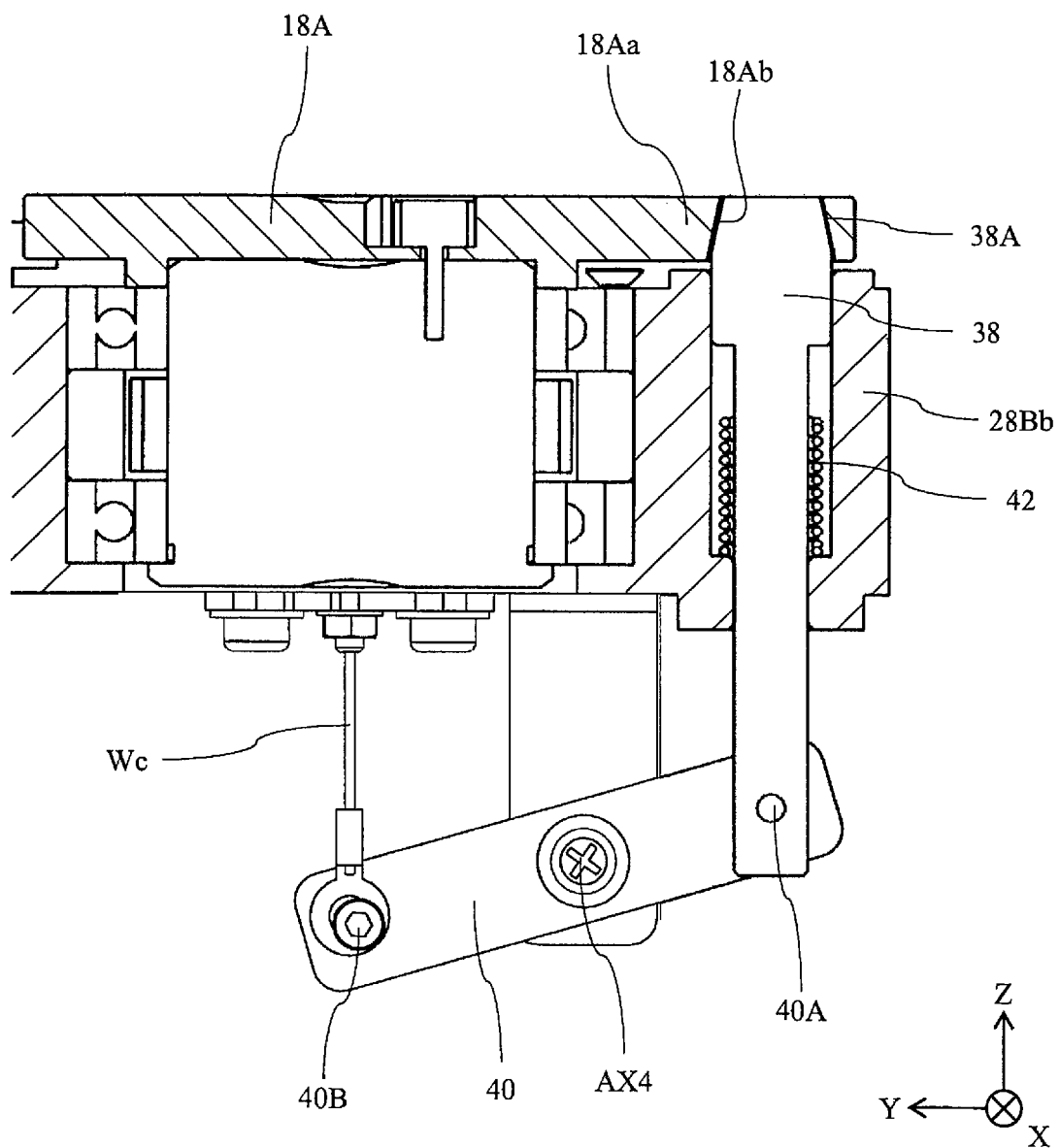
FIG. 7 is a cross sectional view of a second rotation lock mechanism.

FIG. 7 shows a cross-sectional view of a connection between the rotor 18A and the stator 28Bb; that is, a connection between the mounting unit 18 and the slidable plate 28B. A second lock pin 38 is provided below the flange 18Aa. The second lock pin 38 has a vertically-elongated shape and is vertically movable. The tip of the second lock pin 38 is engageable in one of the second-set lock holes 18Ab in the flange 18Aa. FIG. 7 shows the second lock pin 38 engaged in one of the second-set lock holes 18Ab. The engagement of the second lock pin 38 in the second-set lock hole 18Ab restricts the rotational movement of the rotor 18A (thus, that of the mounting unit 18). Accordingly, the second-set lock holes 18Ab and the second lock pin 38 function as the second rotation lock mechanism. Because multiple second-set lock holes 18Ab are provided, the position to lock the mounting unit 18 is selectable from multiple positions (in other words, orientations).

The proximal end (the end opposite to the flange 18Aa) of the second lock pin 38 is connected to a pin connector 40A of a second relay member 40. In the present embodiment, the pin connector 40A is provided at one end of the second relay member 40. The second relay member 40 has an elongated shape extending in a vertical plane (XY plane) and is rotatably attached to the stator 28Bb such that the second relay member 40 is rotatable in a vertical plane about a horizontal rotation axis AX4 (extending along the X axis; in other words, in a right-left direction). The second lock pin 38 and the second relay member 40 move forward and rearward along with the forward/rearward movement of the slidable plate 28B (and the mounting unit 18). A wire Wc is connected to a wire connector 40B of the second relay member 40. In the present embodiment, the wire connector 40B is provided at the opposite side of the second relay member 40 from the pin connector 40A. Similarly to the wires Wa and Wb, the wire Wc extends to the actuator 22. The wire Wc passes through a central through-hole of the rotor 18A (and the hole of the stator 28Bb) to the actuator 22 on the mounting unit 18.

When the wire Wc is pulled upward, the second relay member 40 rotates clockwise in FIG. 7; in other words, the pin connector 40A moves downward. As a result, the second lock pin 38 moves downward; that is, in the direction away from the flange 18Aa such that the engagement of the second lock pin 38 in the second-set lock hole 18Ab is released and the restriction of the rotational movement of the rotor 18A (thus, that of the mounting unit 18) is released. The second lock pin 38 is urged upward toward the flange 18Aa by a spring 42. Accordingly, when no pulling force is applied to the wire Wc, the urging force of the spring 42 moves the second lock pin 38 upward such that the second lock pin 38 engages in one of the second-set lock holes 18Ab to lock the rotational movement of the mounting unit 18.

A lateral wall of each second-set lock hole 18Ab may include a tilted portion such that the diameter of the hole becomes gradually larger toward the bottom opening. Correspondingly, the lateral surface of the tip of the second lock pin 38 may include a tapered portion 38A whose diameter becomes gradually smaller from the proximal end toward the distal end. In engagement, the tapered portion 38A of the second lock pin 38 opposes the lateral-wall tilted portion of the second-set lock hole 18Ab. This reduces possible friction between the lateral surface of the second lock pin 38 and the lateral-wall tilted portion of the second-set lock holes 18Ab when the tip of the second lock pin 38 pulls out of the second-set lock hole 18Ab. As a result, the required force to pull the wire Wc to release the lock of the second rotational movement is reduced. Furthermore, the lateral-wall tilted portion of the second-set lock holes 18Ab and the tapered portion 38A of the second lock pin 38 are also advantageous in reducing instability of the mounting unit 18 with respect to the slidable plate 28B when locked. This further reduces instability of the operation panel 16, improving operability of the operation panel 16.

Similar to the first-set lock holes 26Aa, the second-set lock holes 18Ab may include lateral-wall non-tilted portions in front of and behind the lateral-wall tilted portion. The lateral-wall non-tilted portions may extend along a hole depth direction to define a constant hole diameter. Similar to the first lock pin 34, the lateral surface of the second lock pin 38 may include straight portions on the proximal and distal sides of the tapered portion 38A (refer to FIG. 5).

In order to reduce the required force to pull the wire Wc in order to release the lock of the second rotational movement, in the second relay member 40, the distance between the wire connector 40B and the rotation axis AX4 may be made longer than the distance between the pin connector 40A and the rotation axis AX4. In this way, the required force to pull the wire Wc in order to release the second rotational movement (in other words, to move the second lock pin 38) can be reduced based on the lever principle.

Figure 8:
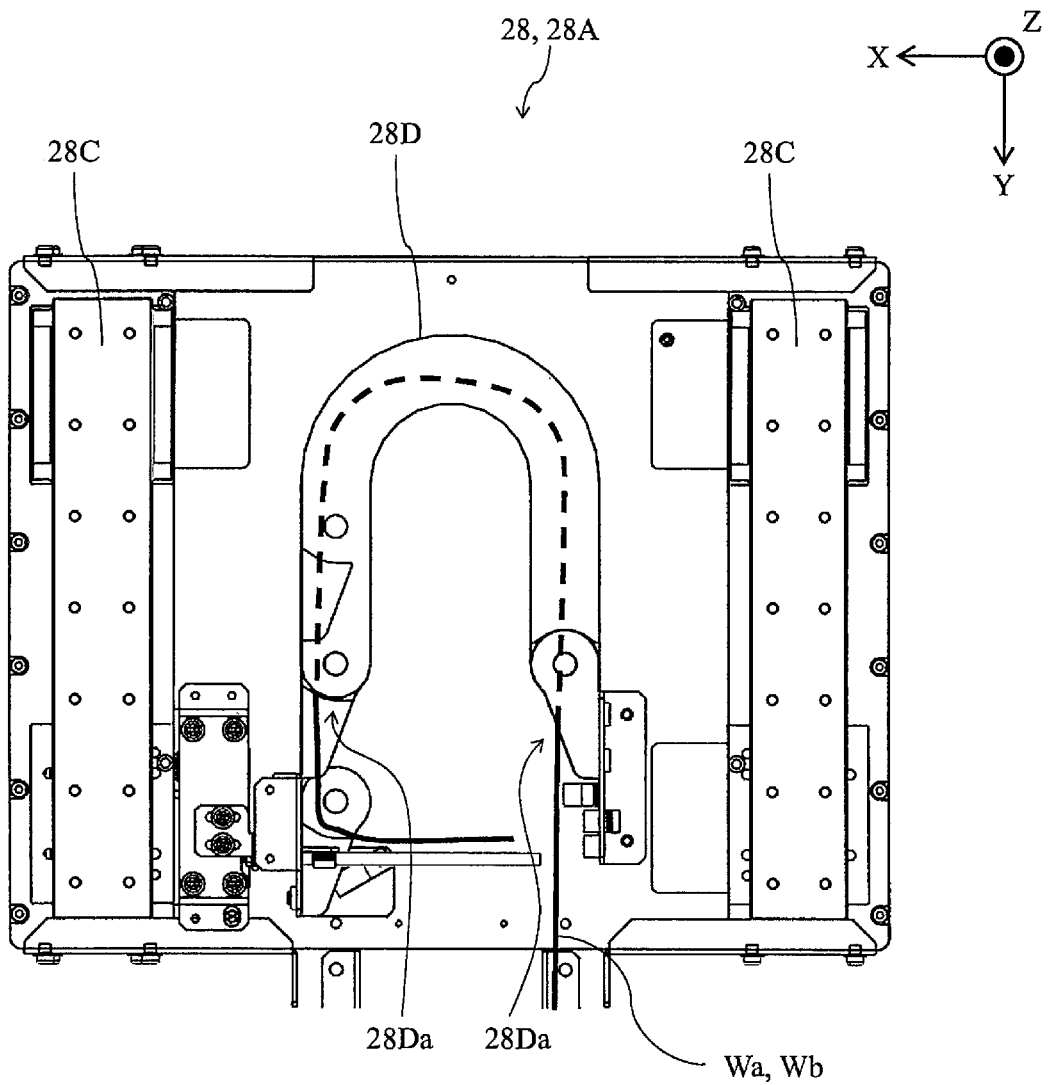
FIG. 8 is a plan view showing an internal structure of the movable base.

FIG. 8 is a plan view of the movable base 28. In FIG. 8, the lower side is the rear and the upper side is the front. The slidable plate 28B is omitted in FIG. 8. Thus, FIG. 8 is a plan view of the box body 28A, in which two rails 28C, each extending in a front-rear direction, are provided respectively on the right and left. Two corresponding grooves (not shown) which extend in a front-rear direction and engage with the rails 28C are provided respectively on the right and left of the bottom surface of the slidable plate 28B. With the grooves of the slidable plate 28B engaged with the rails 28C, the slidable plate 28B is slidably attached to the box body 28A such that the slidable plate 28B can be moved in the front-rear direction with respect to the box body 28A.

Figure 9:
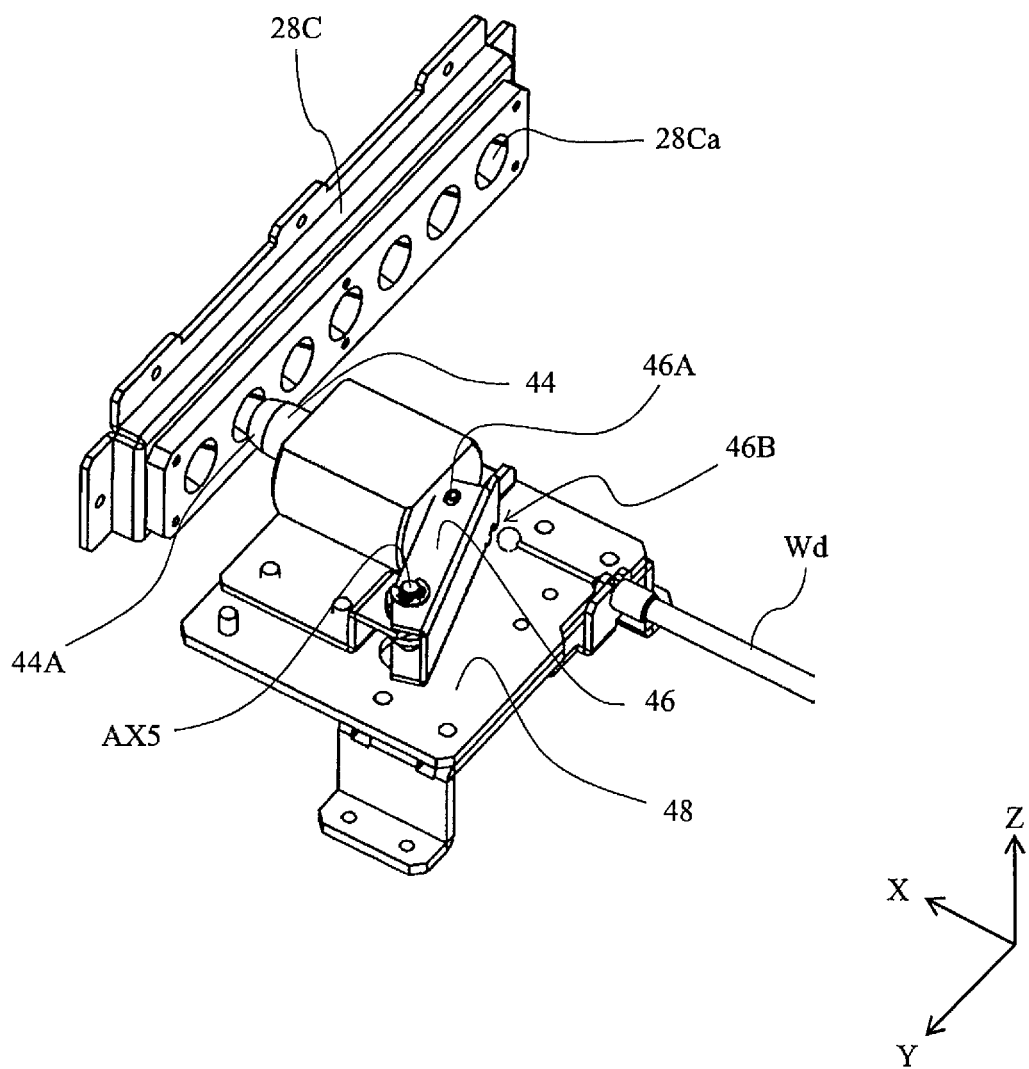
FIG. 9 is a perspective view of a front-rear lock mechanism.

FIG. 9 is a perspective view of a front-rear lock mechanism which locks the front-rear movement of the slidable plate 28B. Multiple third-set lock holes 28Ca are aligned along the front-rear direction in the inner side surface (the left side surface, which is on the right in FIG. 8) of the right rail 28C (on the left in FIG. 8) in the box body 28A.

A third lock pin 44 is provided on the side of the right rail 28C which includes the third-set lock holes 28Ca. The third lock pin 44 has an elongated shape which extends along a right-left direction such that the third lock pin 44 is movable along the right-left direction. The tip of the third lock pin 44 is thus engageable with one of the third-set lock holes 28Ca on the side surface of the rail 28C. The engagement of the third lock pin 44 in the third-set lock hole 28Ca restricts the front-rear movement of the slidable plate 28B. The third-set lock holes 28Ca and the third lock pin 44 function as a front-rear lock mechanism.

The third lock pin 44 is attached to a base 48 via a third relay member 46 described in detail below. The base 48 is attached to the slidable plate 28B. Accordingly, the third lock pin 44, the third relay member 46, and the base 48 move unitedly with the slidable plate 28B. Because multiple third-set lock holes 28Ca are provided in the front-rear direction on the side surface of the rail 28C which extends in the front-rear direction, the position to lock the slidable plate 28B is selectable from the multiple positions.

The proximal end (the end opposite to the rail 28C) of the third lock pin 44 is connected to a pin connector 46A of the third relay member 46. The third relay member 46 has an elongated shape along a horizontal direction and is rotatably attached to the base 48 such that the third relay member 46 is rotatable in a horizontal plane about a vertical rotation axis AX5. A wire Wd is connected to a wire connector 46B of the third relay member 46. In the present embodiment, the rotation axis AX5 is disposed at one end of the third relay member 46, while the wire connector 46B is disposed at the other end of the third relay member 46. The pin connector 46A is disposed between the rotation axis AX5 and the wire connector 46B.

Similarly to the wires Wa to Wc, the wire Wd extends to the actuator 22. Similarly to the wire Wc, the wire Wd passes through the central through-hole of the rotor 18A of the mounting unit 18 to the actuator 22 of the mounting unit 18 (and the hole of the stator 28Bb of the slidable plate 28B) (refer to FIG. 6).

When the wire Wd is pulled to the left (to the lower right in FIG. 9), the third relay member 46 rotates clockwise in FIG. 9, and thus, the pin connector 46A moves leftward (rightward in FIG. 9). Because the third lock pin 44 moves to the left; that is, in the direction away from the rail 28C, the engagement of the third lock pin 44 in the third-set lock holes 28Ca is released and the restriction of the front-rear movement of the slidable plate 28B is released. The third lock pin 44 is urged toward the rail 28C by a spring (not shown). Accordingly, when no pulling force is applied to the wire Wd, the urging force of the spring moves the third lock pin 44 toward the rail 28C such that the third lock pin 44 engages in one of the third-set lock holes 28Ca to restrict the front-rear movement of the slidable plate 28B.

A lateral wall of each third-set lock hole 28Ca may include a lateral-wall tilted portion such that the diameter of the hole becomes gradually larger toward the opening. Correspondingly, the lateral surface of the tip of the third lock pin 44 may include a tapered portion 44A whose diameter becomes gradually smaller from the proximal end toward the distal end. In engagement, the tapered portion 44A of the third lock pin 44 opposes the lateral-wall tilted portion of the third-set lock hole 28Ca. This reduces friction between the lateral surface of the third lock pin 44 and the lateral wall of the third-set lock hole 28Ca when the tip of the third lock pin 44 pulls out of the third-set lock hole 28Ca. As a result, the required force to pull the wire Wd in order to release the lock of the front-rear movement is reduced. Furthermore, the lateral-wall tilted portion of the third-set lock holes 28Ca and the tapered portion 38A of the third lock pin 44 are also advantageous in reducing instability of the slidable plate 28B with respect to the box body 28A when locked. This further reduces instability of the operation panel 16, improving operability of the operation panel 16.

Similarly to the first-set lock holes 26Aa, the lateral wall of each third-set lock hole 28Ca may include lateral-wall non-tilted portions in front of and behind the lateral-wall tilted portion. The lateral-wall non-tilted portions may extend along a hole depth direction to define a constant hole diameter. Correspondingly, the lateral surface of the third lock pin 44 may include straight portions on the proximal and distal sides of the tapered portion 44A, similarly to the first lock pin 34 (refer to FIG. 5).

In the present embodiment, because the distance from the pin connector 46B to the rotation axis AX5 is longer than the distance from the wire connector 46A to the rotation axis AX5, the required force to pull the wire Wd in order to release the lock of the front-rear movement (in other words, to move the third lock pin 44) can be reduced based on the lever principle.

Figure 10:
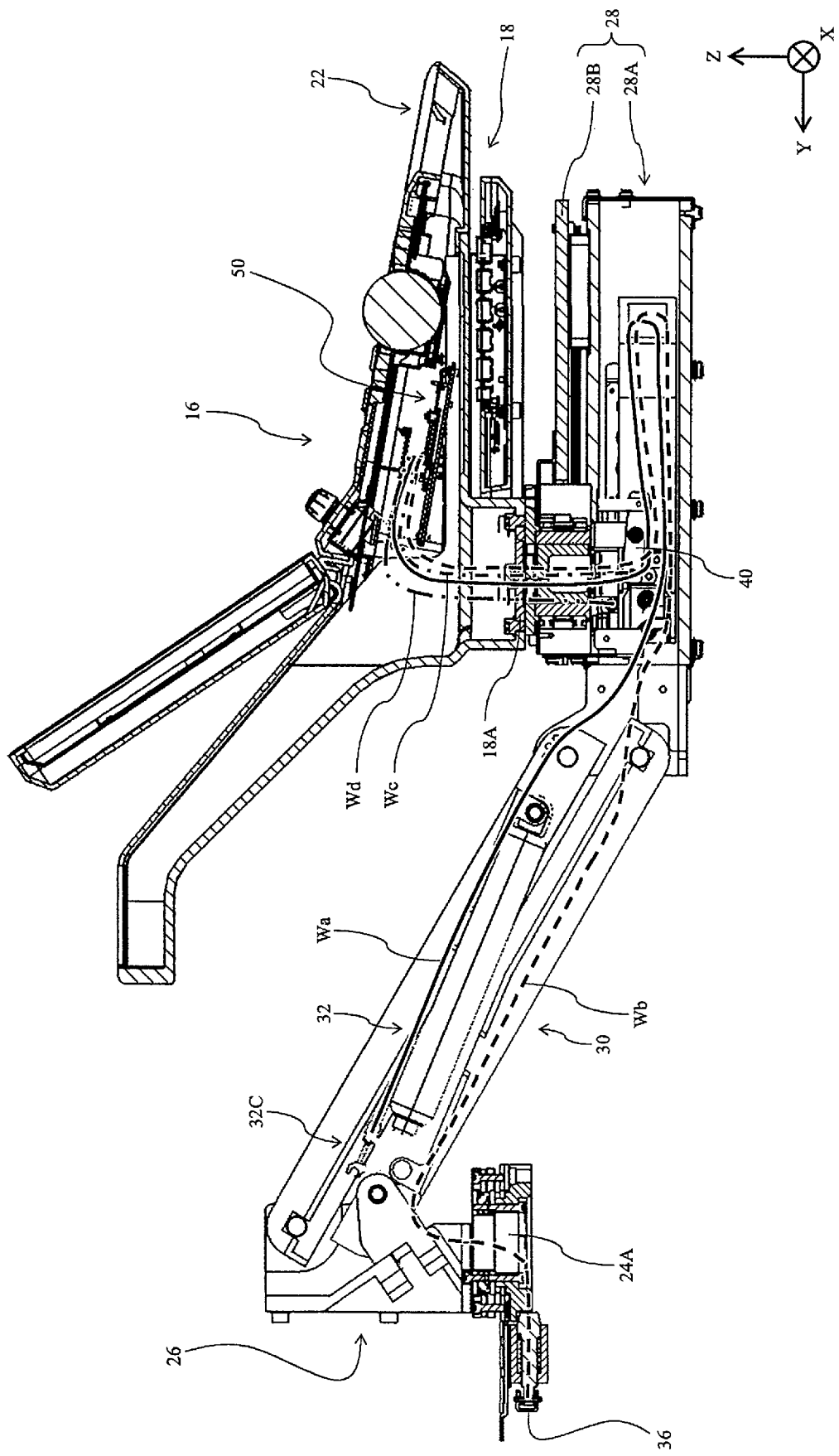
FIG. 10 is a diagram showing paths of respective wires extending from the respective lock mechanisms.

The respective movement mechanisms of the movable support mechanism 20 and the lock mechanisms of these movement mechanisms are described above. FIG. 10 shows the paths of the wires Wa to Wd which extend from the respective lock mechanisms to the actuator 22 of the mounting unit 18.

In FIG. 10, the wire Wa which extends from the lock 32C of the gas spring 32 used as the up-down lock mechanism is shown with a solid line. The wire Wa extends from the lock 32C into the box body 28A of the movable base 28 through the parallel linkage 30, and from the box body 28A to the mounting unit 18 through the central through-hole of the rotor 18A of the mounting unit 18.

The wire Wb which extends from the first relay member 36 to which the first lock pin 34 used as the first rotation lock mechanism is connected is shown with a broken line in FIG. 10. The wire Wb extends from the first relay member 36 into the parallel linkage 30 through the central through-hole of the stator 24A of the fixed pole 24, and passes through the parallel linkage 30 to the box body 28A of the movable base 28 and then into the mounting unit 18 through the central through-hole of the rotor 18A of the mounting unit 18.

The wire Wc which extends from the second relay member 40 to which the second lock pin 38 used as the second rotation lock mechanism is connected is shown with a one-dot chain line in FIG. 10. The wire Wc extends from the second relay member 40 into the mounting unit 18 through the central through-hole of the rotor 18A of the mounting unit 18.

The wire Wd which extends from the third relay member 46 to which the third lock pin 44 used as the front-rear lock mechanism is connected is shown with a two-dot chain line in FIG. 10. The wire Wd extends from the third relay member 46 into the mounting unit 18 through the central through-hole of the rotor 18A of the mounting unit 18.

As described above, the wires Wa to Wd extend inside the movable support mechanism 20 such that, almost entirely, the wires Wa to Wd are not exposed outside.

As shown in FIG. 8, a wire duct 28D is disposed inside the box body 28A. The tubular wire duct 28D is bent in a U-shape in a plan view. At each end, the wire duct 28D has an opening 28Da which faces rearward. The wires Wa and the Wb are disposed in the wire duct 28D. As described above, while the wires Wa and Wb extend into the mounting unit 18 through the central through-hole of the rotor 18A of the mounting unit 18, the rotor 18A is movable forward and rearward with the slidable plate 28B. Accordingly, the paths of the wires Wa and Wb change along with the forward/rearward movement of the slidable plate 28B. Such a change in the path of the wires Wa and Wb along with the forward/rearward movement of the slidable plate 28B may cause the wires Wa and Wb to get caught by any obstruction or become impossible to be pulled smoothly when operating the actuator 22. In order to reduce these risks, the wires Wa and Wb are disposed in the wire duct 28D to allow extra length. By using the U-shaped wire duct 28D, the bending radius R of the wires Wa and Wb may be maintained unchanged when the slidable plate 28B is moved forward or rearward. This reduces a change, along the forward/rearward movement of the slidable plate 28B, in the resistance of the wires Wa and Wb, and thus, in the force required to manipulate the wires Wa and Wb or the required movement distance of the wires Wa and Wb to release the lock.

The wires Wc and Wd also extend into the mounting unit 18 through the rotor 18A. However, because the second relay member 40 to which the wire Wc is connected and the third relay member 46 to which the wire Wd is connected move forward/rearward along with the slidable plate 28B (thus, the rotor 18A), even when the rotor 18A moves forward/rearward, the relative position between the rotor 18A and the second relay member 40 or the third relay member 46 does not change such that the paths of the wires Wc and Wd do not significantly change. For this reason, the wires Wc and Wd are not disposed in the wire duct 28D.

Figure 11:
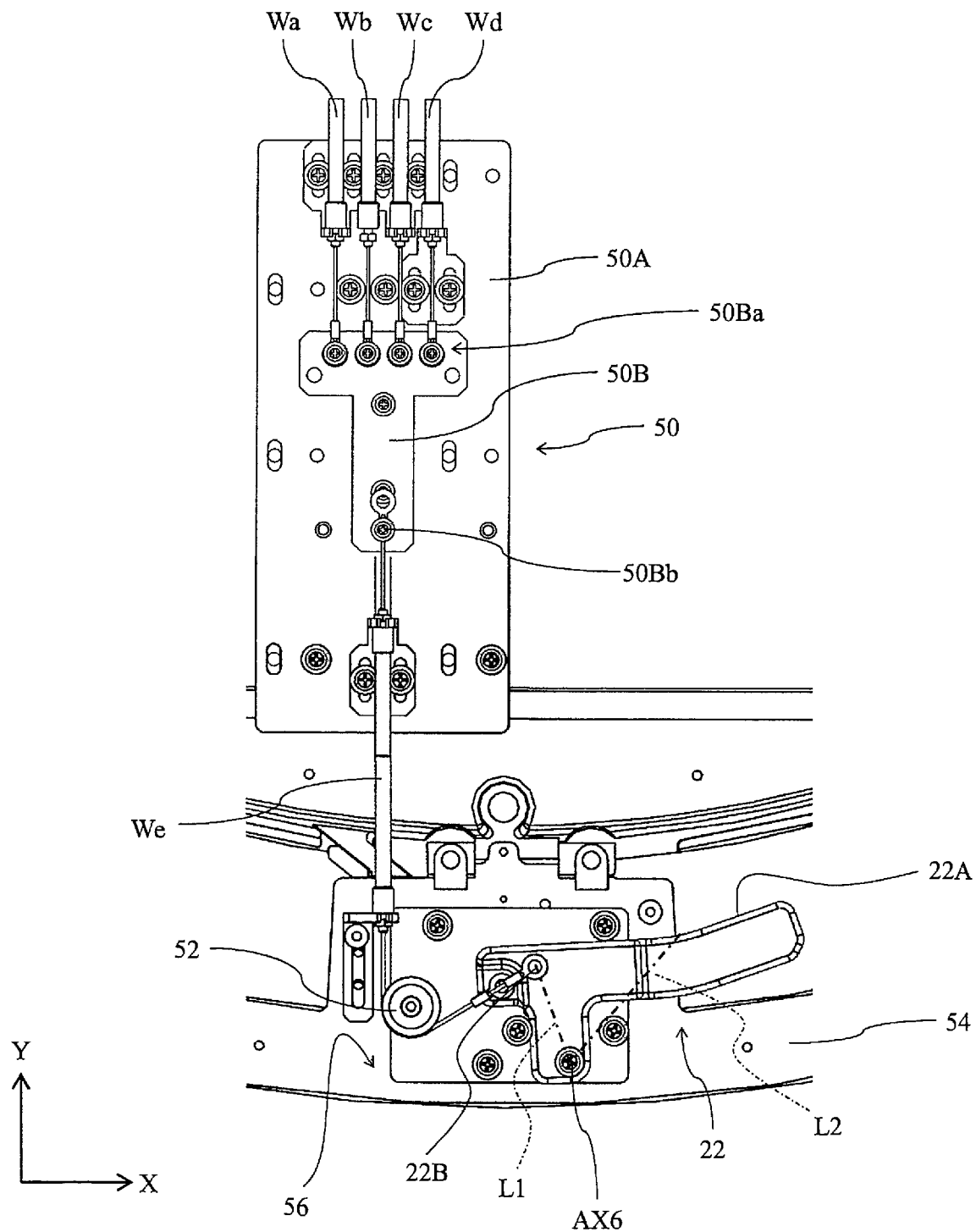
FIG. 11 is a plan view showing an actuator and a wire relay mechanism.

In the present embodiment, the wires Wa to Wd are connected to a wire relay mechanism 50 on the mounting unit 18. FIG. 11 is a plan view of the mounting unit 18, showing the wire relay mechanism 50 and the actuator 22. FIG. 11 omits elements other than the wire relay mechanism 50, the actuator 22, and their related elements.

The wire relay mechanism 50 includes a base 50A fixed on the mounting unit 18 and a movable portion 50B which is movable forward and rearward with respect to the base 50A. The wires Wa to Wd, also referred to as "first section", are connected to a rear end 50Ba of the movable portion 50B. Accordingly, the wire Wa connects the lock 32C (refer to FIG. 3) of the gas spring 32 and the movable portion 50B; the wire Wb connects the first relay member 36 (refer to FIG. 4) and the movable portion 50B; the wire Wc connects the second relay member 40 (refer to FIG. 7) and the movable portion 50B; and the wire Wd connects the third relay member 46 (refer to FIG. 9) and the movable portion 50B.

A wire We, also referred to as "second section", is connected to a front end 50Bb of the movable portion 50B.

The wire We extends forward and is bent by a pulley 52 toward the right and slightly rearward to be connected to the actuator 22.

The actuator 22 is operated by an operator to change the restriction state of the respective lock mechanisms. The actuator 22 is located near to a handle 54 which is disposed along the front edge of the mounting unit 18 in the right-left direction such that the operator can hold the mounting unit 18. In the present embodiment, a palm rest 56 (a cover of the palm rest 56 is not shown in FIG. 11, and an inner view is shown) on which the operator can rest the operator's palm or around the wrist is disposed at the lateral center of the handle 54. The actuator 22 is partially under the palm rest 56.

In the present embodiment, the actuator 22 includes a long portion which extends along the right-left direction and a short portion which extends in the front-rear direction from the left end of the long portion. The combination of the long portion and the short portion of the actuator 22 forms a substantial L shape in a plan view. A right end of the long portion protrudes from under the palm rest 56 to be exposed. This protruded portion is used as a force input portion 22A to which an operator can apply a force. A wire connector 22B to which the wire We from the wire relay mechanism 50 (the movable portion 50B) is connected is located at the left end of the long portion of the actuator 22 near the rear edge. The actuator 22 is rotatably attached to the mounting unit 18 such that the actuator 22 is rotatable about a vertical actuator rotation axis AX6 at a front end of the short portion of the actuator 22. When an operator applies a force to the force input portion 22A (specifically, a forward force), the actuator 22 rotates clockwise in a horizontal plane in a plan view about the actuator rotation axis AX6.

When the actuator 22 is rotated, because the wire connector 22B moves rightward, the wire We is pulled rightward such that the movable portion 50B moves forward as the pulley 52 applies a forward force to the movable portion 50B through the wire We. Accordingly, the wires Wa to Wd which are connected to the movable portion 50B are pulled forward. As described above, when the wires Wa to Wd are pulled forward, the restricted states (locked states) of the respective lock mechanisms are released.

In the actuator 22, a distance L1 between the actuator rotation axis AX6 and the wire connector 22B is shorter than a distance L2 between the actuator rotation axis AX6 and the force input portion 22A (at the nearest point to the actuator rotation axis AX6 where an operator can apply a force). This reduces the force required to apply to the force input portion 22A in order to release the restricted state of respective lock mechanisms based on the lever principle.

When the operator releases his/her hand from the actuator 22 (in other words, when the operator stops applying a force to the force input portion 22A), the wires Wa to Wd are pulled rearward by the forces urged by the respective springs of the lock mechanisms. Accordingly, the respective lock mechanisms are placed in the restricted status.

As described above, according to embodiments of the present disclosure, the restriction state of the following four lock mechanisms can be changed through the single actuator 22: the up-down lock mechanism which restricts the up-down movement of the operation panel 16, the first rotation lock mechanism which restricts the first rotational movement of the operation panel 16 about the vertical rotation axis AX1 located away from the operation panel 16, the second rotation lock mechanism which restricts the second rotational movement of the operation panel 16 about the vertical rotation axis AX2 located nearer to the operation panel 16 than is the rotation axis AX1 to the operation panel 16, and the front-rear lock mechanism which restricts the front-rear movement of the operation panel 16. Because the locks are actuated by the wires Wa to We, no electric devices such as an electric motor are used.

When changing the restriction state of multiple lock mechanisms using wires by a single actuator, a strong force to the actuator is assumed to be required. However, when using, in particular, an ultrasonic diagnostic apparatus, an operator is often holding an ultrasonic probe with one of his/her hands and the operator thus must manipulate the actuator with the other hand. Accordingly, it is often the case that the operator can only apply a force as weak as a grip strength. In the present embodiment, because the lock mechanisms are arranged to reduce the force required to release the restricted state of the lock mechanism, a force required to be applied to the actuator 22 by an operator is reduced.

Figure 12:
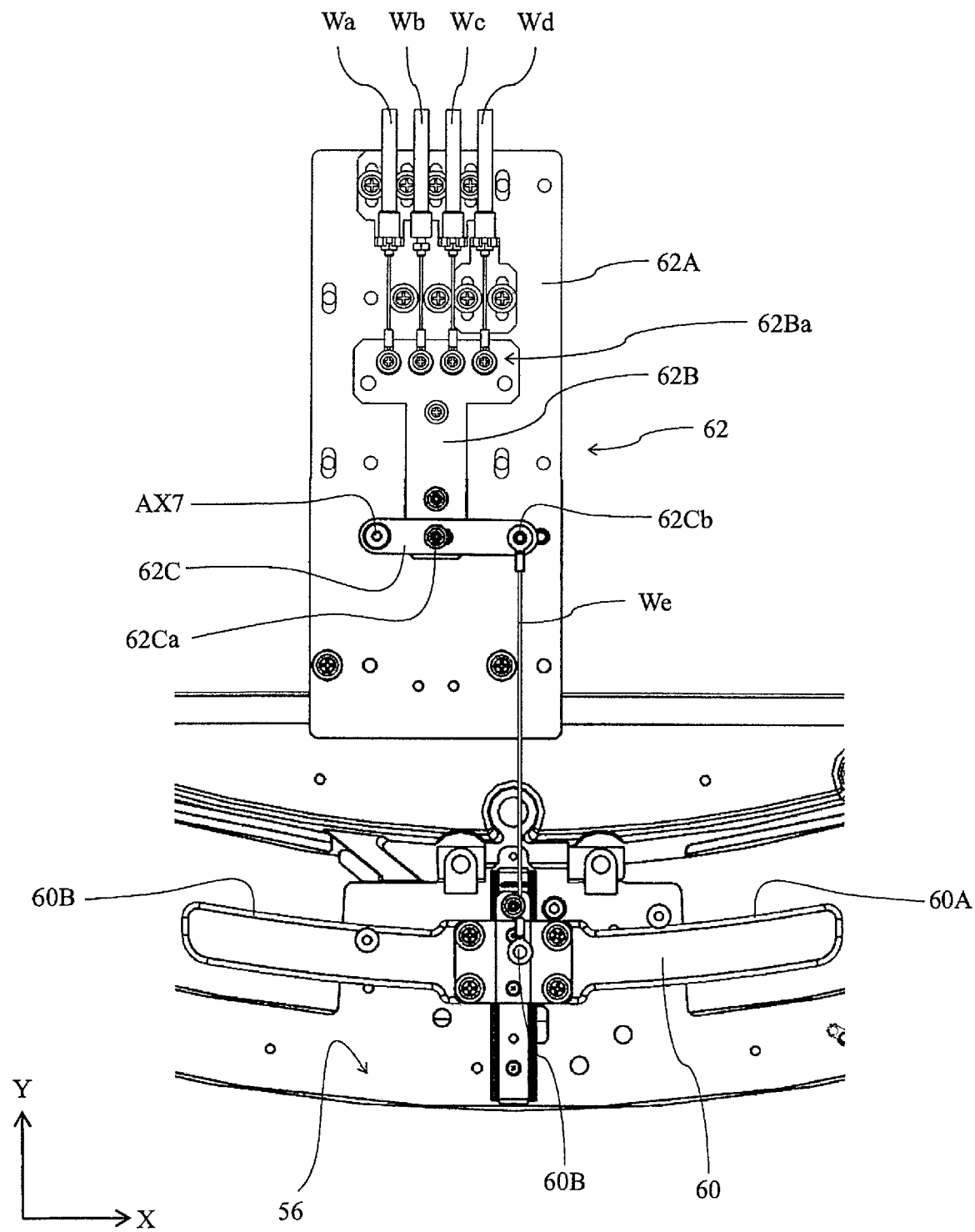
FIG. 12 is a plan view showing a variant embodiment of the actuator and the wire relay mechanism.

FIG. 12 shows a variant embodiment of the actuator and the wire relay mechanism. Similarly to FIG. 11, FIG. 12 omits elements other than an actuator 60, a wire relay mechanism 62, and their related elements.

The actuator 60 according to this variant embodiment has a shape extending in a right-left direction. The right end of the actuator 60 extends rightward from under the palm rest 56 to be exposed, while the left end of the actuator 60 extends leftward from under the palm rest 56 to be exposed. The protruding right and left ends are force input portions 60A to which an operator can apply a force. In this variant embodiment, the operator can grab the right and left force input portions 60A with both hands. Alternatively, the operator may apply a forward force to either one of the right and left force input portions 60A. For example, when the operator holds an ultrasonic probe with one hand, the operator must operate the force input portion 60A with the other hand. In such a case, the operator can operate either one of the right and left force input portions 60A which is more convenient. A wire connector 60B to which the wire We from the wire relay mechanism 62 is connected is located around the lateral center of the actuator 60. When a forward force is applied to the force input portion 60A, the entire actuator 60 moves forward.

Also in the variant embodiment, the wire relay mechanism 62 includes a base 62A fixed on the mounting unit 18 and a movable portion 62B which is movable forward/rearward with respect to the base 62A. The wires Wa to Wd are connected to a rear end 62Ba of the movable portion 62B.

In this variant embodiment, a movable portion connector 62Ca of a fourth relay member 62C which extends in the width direction is attached to the front end of the movable portion 62B. The fourth relay member 62C is rotatably attached to the base 62A such that the fourth relay member 62C is rotatable about a rotation axis AX7 located at the left end of the fourth relay member 62C. The wire We from the actuator 60 is connected to a wire connector 62Cb at the right end of the fourth relay member 62C. In other words, the movable portion connector 62Ca is located between the rotation axis AX7 and the wire connector 62Cb.

When the wire We is pulled forward, the fourth relay member 62C rotates clockwise in FIG. 12 such that the movable portion connector 62Ca moves forward. The movable portion 62B is thus moved forward such that the wires Wa to Wd which are connected to the movable portion 62B are pulled forward. When the wires Wa to Wd are pulled forward, the restricted states (locked states) of the respective lock mechanisms are released.

In the variant embodiment, because the actuator 60 is moved in parallel to itself, the actuator 60 cannot be arranged to reduce the force required to release the restricted states of the respective lock mechanisms. Accordingly, in the variant embodiment, the force required to release the restricted states of the respective lock mechanisms is reduced using the fourth relay member 62C of the wire relay mechanism 62. Specifically, the required force to pull the wire We in order to release the restricted state of the respective lock mechanisms is reduced by making the distance from the wire connector 62Cb to the rotation axis AX7 longer than the distance from the movable portion connector 62Ca to the rotation axis AX7, based on the lever principle.

The fourth relay member 62C used in the variant embodiment may be applied to the basic wire relay mechanism 50 shown in FIG. 11.

Although embodiments of an ultrasonic diagnostic apparatus according to the present disclosure are described above, the ultrasonic diagnostic apparatuses according to the present disclosure are not limited to those described above. Various changes may be applied within the scope of the present disclosure.

For example, although the parallel linkage 30 is used as the up-down movement mechanism which performs the up-down movement of the operation panel 16, for example, the rotary pole 26 may be arranged to be vertically movable along the fixed pole 24 and used as the up-down movement mechanism. The rotary pole 26 and the movable base 28 may be connected through an unmovable arm member. Also in such a case, the gas spring 32 may still be used as the up-down lock mechanism which restricts the up-down movement of the up-down movement mechanism.

The invention claimed is:

1. An ultrasonic diagnostic apparatus comprising:
an operation panel which receives an instruction input from an operator;
a rotary pole which extends vertically at a location away from the operation panel, and which performs a first rotational movement in which the operation panel is rotated in a horizontal plane, by the rotary pole being rotated;
two elongated parallel linkages which support the operation panel, each of the parallel linkages having one end attached to the rotary pole and another end connected to a box body which supports the operation panel, and which performs an up-down movement to change a height of the operation panel;
a slidable plate which is disposed above the box body, which performs a forward-rear movement in which a forward-rear position of the operation panel is changed, by the slidable plate being moved forward and backward with respect to the box body, the slidable plate including a stator disposed in a cut out of the slidable plate;
a mounting unit, on which the operation panel is disposed, which is rotatably attached to the slidable plate via the stator, the mounting unit performing a second rotational movement in which the operation panel is rotated in a horizontal plane, by the mounting unit being rotated with respect to the slidable plate;
an up-down lock mechanism which restricts the up-down movement by the parallel linkage;
a first rotation lock mechanism which restricts the first rotational movement;
a second rotation lock mechanism which restricts the second rotational movement;
a front-rear lock mechanism which restricts the front-rear movement;
an actuator; and
a plurality of wires which respectively connect the actuator and the up-down lock mechanism, the first rotation lock mechanism, the second rotation lock mechanism, and the front-rear lock mechanism,
wherein when the actuator is manipulated by the operator, restriction states of the up-down lock mechanism, the first rotation lock mechanism, the second rotation lock mechanism, and the front-rear lock mechanism are changed by the plurality of wires.

2. The ultrasonic diagnostic apparatus according to claim 1,
wherein the plurality of wires comprise a first section and a second section, the first section comprising at least two wires, of the plurality of wires, respectively connecting the up-down lock mechanism, the first rotation lock mechanism, the second rotation lock mechanism, and the front-rear lock mechanism and a wire relay mechanism, and the second section comprising a single wire, of the plurality of wires, connecting the wire relay mechanism and the actuator.

3. The ultrasonic diagnostic apparatus according to claim 2,
wherein the actuator has a shape extending in a right-left direction, comprises a wire connector to which one of the plurality of wires is connected and right and left force input portions which are provided on the right and left of the wire connector, and the actuator is moved in a front-rear direction by a force applied to at least one of the force input portions by the operator.

4. The ultrasonic diagnostic apparatus according to claim 1, wherein the actuator comprises a wire connector to which one of the plurality of wires is connected and a force input portion to which the operator applies a force, wherein the actuator rotates about an actuator rotation axis by a force applied to the force input portion by the operator, and
wherein a distance between the actuator rotation axis and the wire connector is shorter than a distance between the actuator rotation axis and the force input portion.

5. The ultrasonic diagnostic apparatus according to claim 1,
wherein at least one of the first rotation lock mechanism, the second rotation lock mechanism, or the front-rear lock mechanism comprises a lock hole and a lock pin which restricts a movement by engaging with the lock hole,
wherein a lateral wall of the lock hole comprises a lateral-wall tilted portion which is tilted such that the diameter of the lock hole becomes gradually larger toward an opening, and
wherein a lateral surface of the lock pin comprises a tapered portion which opposes the lateral-wall tilted portion of the lock hole.

6. The ultrasonic diagnostic apparatus according to claim 5,
wherein the lateral wall of the lock hole comprises at least two lateral-wall non-tilted portions extending along a lock hole depth direction with a constant diameter, each of the at least two lateral-wall non-tilted portions being disposed in front of and behind the lateral-wall tilted portion, and
wherein the lateral surface of the lock pin comprises at least two straight portions opposing the lateral-wall non-tilted portions in engagement, each of the at least two straight portions being disposed on a proximal side or distal side of the tapered portion.

7. The ultrasonic diagnostic apparatus according to claim 1,
wherein a surface area of the slidable plate is greater than that of the mounting unit, and
wherein the up-down lock mechanism has one end attached to one of the two elongated parallel linkages and another end attached to the other of the two elongated parallel linkages.

8. The ultrasonic diagnostic apparatus according to claim 1,
wherein a surface area of an upper surface of the slidable plate is greater than a surface area of an upper surface of the stator.

* * * * *